US012653394B2

(12) United States Patent
Fangmann et al.

(10) Patent No.: US 12,653,394 B2
(45) Date of Patent: Jun. 16, 2026

(54) SURGICAL LARYNGOSCOPE BLADE AND METHOD OF MANUFACTURE

(71) Applicant: KARL STORZ SE & Co. KG, Tuttlingen (DE)

(72) Inventors: Johannes Fangmann, Friedrichshafen-Kluftern (DE); Kamilla König-Urban, Tuttlingen (DE); Fabienne Riester, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 177 days.

(21) Appl. No.: 18/589,070

(22) Filed: Feb. 27, 2024

(65) Prior Publication Data

US 2024/0285161 A1      Aug. 29, 2024

(30) Foreign Application Priority Data

Feb. 27, 2023      (DE) ......................... 102023104782.5

(51) Int. Cl.
A61B 1/267          (2006.01)
A61B 1/00          (2006.01)
(Continued)

(52) U.S. Cl.
CPC .......... A61B 1/2673 (2013.01); A61B 1/0011 (2013.01); A61B 1/07 (2013.01); A61B 1/32 (2013.01)

(58) Field of Classification Search
None
See application file for complete search history.

(56) References Cited

U.S. PATENT DOCUMENTS 3,986,854 A      10/1976   Scrivo
4,556,052 A  *  12/1985   Muller ................... A61B 1/267
                                                                600/199
(Continued)

FOREIGN PATENT DOCUMENTS

FR          2478458 A1      9/1981

OTHER PUBLICATIONS

Putz, German Examination Report, Jan. 25, 2024, pp. 1-18, DPMA, Munich. (English translation appended).
(Continued)

*Primary Examiner* — Tessa M Matthews
(74) *Attorney, Agent, or Firm* — David N. Villalpando; Jason Worgull; Jacqueline Cohen

(57)          ABSTRACT
A surgical laryngoscope blade made of a metallic base material with a shaft having an elongate base body is presented. The base body extends between a proximal and distal end and forms a central main channel and an auxiliary channel. The main channel comprises a proximal end profile and a distal end profile. The proximal end profile has an approximately oval design. The distal end profile is geometrically adapted to a vocal cord apparatus. The major axis of the proximal end profile and the major axis of the distal end profile are oriented orthogonal to one another. The auxiliary channel is spaced apart from the main channel in a proximal end region adjacent to the proximal end of the base body. The auxiliary channel opens into the main channel in a distal end region. A method serves to produce such a surgical laryngoscope blade.

20 Claims, 5 Drawing Sheets

Figure 1:
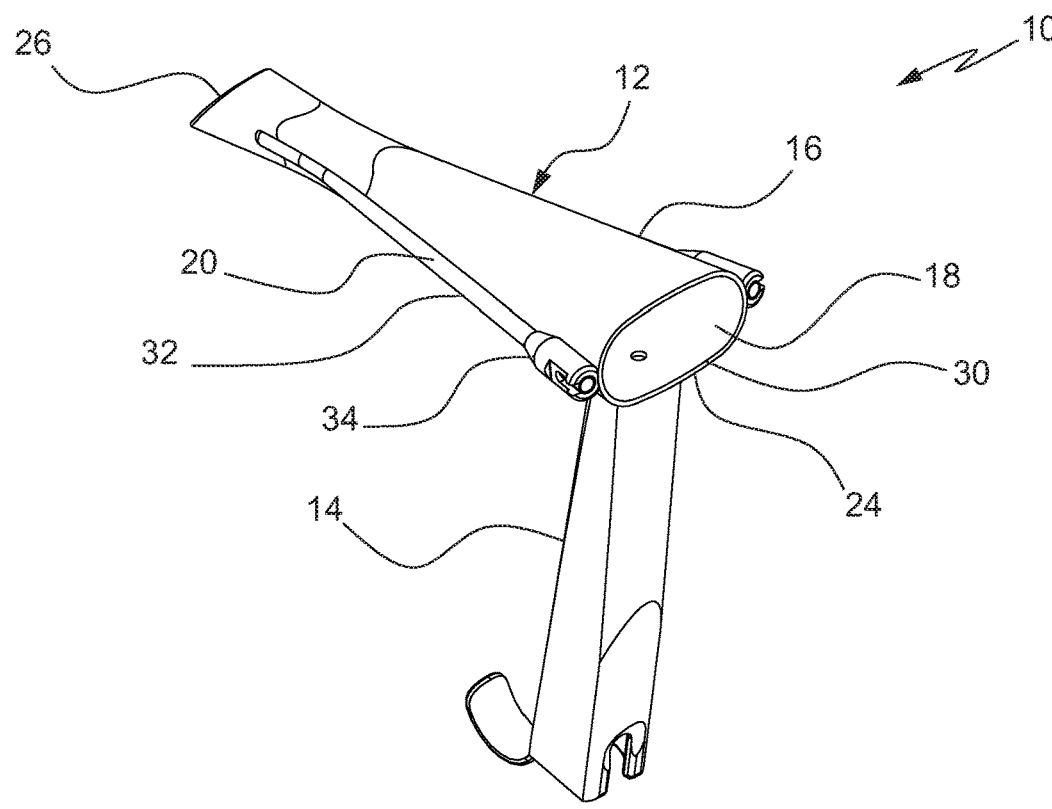

(51) Int. Cl.
_A61B 1/07_ (2006.01)
_A61B 1/32_ (2006.01)

(56) References Cited

U.S. PATENT DOCUMENTS

| | | | | | |
|---|---|---|---|---|---|
| 4,877,016 | A | * | 10/1989 | Kantor | A61B 1/042 |
| | | | | | 600/128 |
| 5,402,771 | A | | 4/1995 | Pilling | |
| 2012/0283513 | A1 | * | 11/2012 | Leeflang | A61M 16/208 |
| | | | | | 600/114 |
| 2020/0113427 | A1 | * | 4/2020 | Molnar | A61M 16/0463 |
| 2020/0113698 | A1 | | 4/2020 | Herzog et al. | |

OTHER PUBLICATIONS

Karl Storz Se & Co., KG, Endoscopes and Instruments for ENT
Esophagoscopy-Bronchoscopy, pp. 1-3 and 424-448, Jan. 2023,
Karl Storz Se & Co., KG, Germany.

* cited by examiner

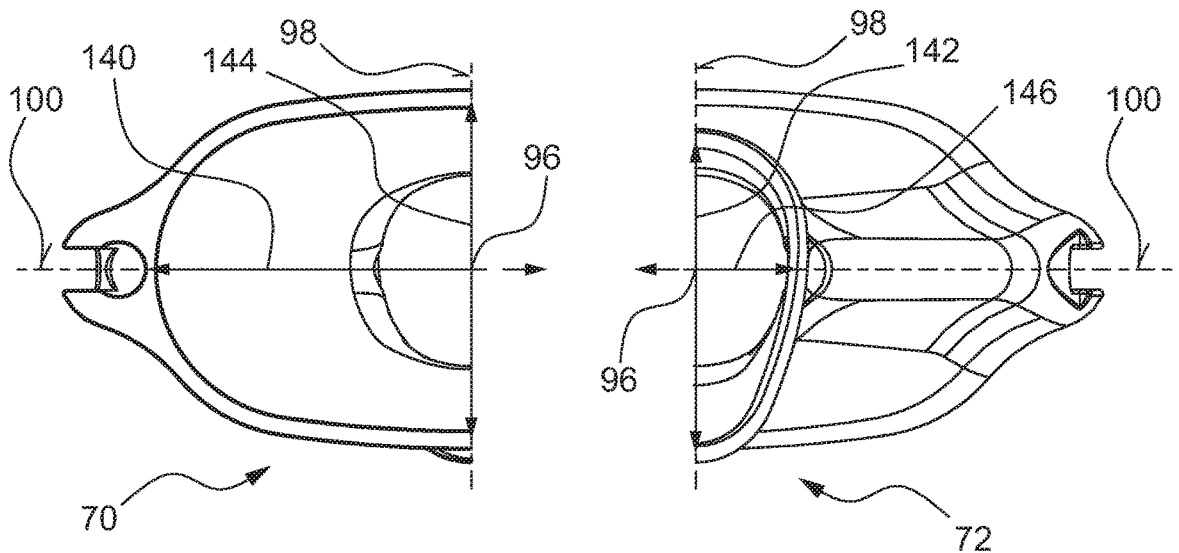
Fig. 6
Fig. 7
Fig. 8
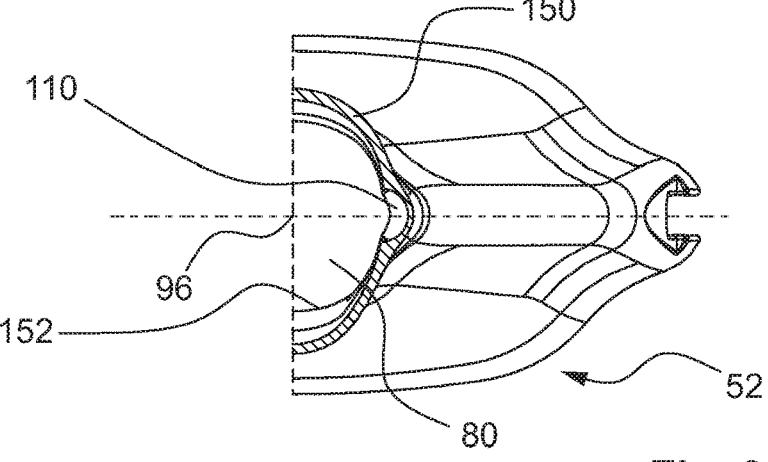
Fig. 9

S10

S12

S14

S16

SURGICAL LARYNGOSCOPE BLADE AND METHOD OF MANUFACTURE

The present disclosure considers medical instruments and components, especially those used to provide access to the body interior, and their production. In particular, the present disclosure considers the design and production of blades for what are known as surgical laryngoscopes.

Operating laryngoscopes are medical instruments usually used to observe and treat the larynx. Laryngeal microsurgery is a usual application. On account of a tubular design of the blade, surgical laryngoscopes allow direct observation of the larynx or vocal cords. Surgical laryngoscopes usually provide further functions, at least comprising the illumination of the observed region (for example the larynx). The shaft of surgical laryngoscopes usually consists of metal materials. As a rule, surgical laryngoscopes are not disposable instruments. In this respect, surgical laryngoscopes differ from disposable laryngoscopes which are used for intubation in emergency medicine, for example. Disposable laryngoscopes usually comprise a blade that is discarded after use. For example, the blades of disposable laryngoscopes are formed from plastics.

A conventional surgical laryngoscope usually consists of a plurality of components that must be processed and interconnected with great effort. This comprises, firstly, complicated subtractive machining and, secondly, relatively complicated joining processes. Different method steps are required, leading to a significant production time. Time-consuming manual work steps are frequently also required. For example, the joints are frequently visible, and so complicated post-processing might be required.

Very different regulatory directions must be satisfied for the use as a medical instrument; for example, the so-called medical device regulation is applicable within the European Union. This significantly increases the outlay for documentation and validation as the number of components used and number of different manufacturing steps increases. This applies all the more if manual manufacturing steps are required.

Established manufacturing processes for blades for surgical laryngoscopes contain a large number of manual process steps, which have effects on the production time and the quality of the end product. On the one hand, this is due to the number of individual parts required. Optionally, grinding processes, soldering processes and/or welding processes are required with regards to the needed process steps and processing. This usually requires a design of the instrument suitable for manufacturing, wherein compromises may have to be accepted with regards to usability, patient tolerance and functionality under certain circumstances.

Against this background, the present disclosure is based on the object of specifying an integrally designed blade for a surgical laryngoscope which is optimized with regards to application and patient tolerance, and which can also be produced efficiently. In particular, the blade should preferably provide an optimized function which is to the benefit of the specialist medical staff and the patient. Optionally, this comprises an anatomically advantageous design and good handling. During use, the instrument should behave as atraumatically as possible.

The production should be implemented in accordance with a method suitable to this end, which enables functional integration and component integration. The production should be implemented in as few steps as possible and should enable a design adapted to the use purpose, especially also in relation to the cleaning and preparation of the instrument. Further, the outlay for the production of the instrument (for example the unit costs) should be reduced, especially also in relation to the additional manual outlay. Moreover, the instrument should be producible with repetitive accuracy and process reliability.

According to a first aspect, the present disclosure relates to an integrally designed surgical laryngoscope blade made of a metallic base material, having a shaft with an elongate base body which extends between a proximal end and a distal end and which forms a central main channel and at least one auxiliary channel that is usable as a light guide channel, wherein the main channel comprises a proximal end profile at the proximal end and a distal end profile at the distal end, wherein the proximal end profile has an at least approximately oval design, wherein the distal end profile is geometrically adapted to the vocal cord apparatus, wherein the proximal end profile has a major axis, wherein the distal end profile has a major axis, wherein the major axis of the proximal end profile and the major axis of the distal end profile are oriented orthogonal to one another, and wherein the at least one auxiliary channel is spaced apart from the main channel in a proximal end region adjacent to the proximal end of the base body and opens into the main channel in a distal end region adjacent to the distal end.

The problem addressed by the disclosure is solved in this way. In particular, the surgical laryngoscope blade is an additively manufactured blade based on a metal material. In particular, the surgical laryngoscope blade is designed in one piece.

Additive manufacturing (AM) allows an optimization of the component overall, with this being traced back, for example, to the integration of a plurality of functions and to the avoidance of assembly transitions. In an exemplary configuration, the blade is designed integrally and manufactured integrally.

The base body predominantly forms the main channel but also the at least one secondary channel. The main channel comprises a first specific profile (proximal end profile) at the proximal end and a second specific profile (distal end profile) at the distal end. Further, at least exemplary configurations contain a third specific profile which is located along the longitudinal extent of the main channel and which allows a transition between the proximal end profile and the distal end profile. The third specific profile may be referred to as transition profile or minimum profile. In an exemplary configuration, the third specific profile along the longitudinal extent is the profile with the smallest cross-sectional area ("waist") of the main channel. For example, the third specific profile is approximately circular such that a harmonious transition between the proximal end profile and the distal end profile is rendered possible.

Integral manufacturing for example allows a variation in the wall thickness along the longitudinal extent of the component, with the result that it is possible to, firstly, optimize the weight and material requirements and, at the same time, provide a particularly patient-safe atraumatic design.

Integral manufacturing avoids joining processes and the necessity to provide individual parts, and so it is also possible to improve the economic efficiency overall. Further, this increases the capabilities for individualization. If need be, components can be adapted to specific patients or patient groups in a targeted manner.

For example, surgical laryngoscopes can be used in ears, nose and throat medicine for inspecting and performing procedures on the larynx. In this context, these are reusable surgical laryngoscopes, and hence not disposable parts.

Thus, the scope of the present disclosure is not restricted to proposing a change in manufacturing method. Additionally, this also relates to a functional optimization. Further advantages can be achieved in this way, for example a weight optimization and the integration of various functions and components. To the extent that it is possible to make do without complicated assembly steps/joining steps/processing steps, it is possible overall to increase the quality of the components and the economic efficiency during the production.

The design optimization is made possible by switching the manufacturing method. Overall, this enables the creation of a blade for a surgical laryngoscope, the cross section and wall thickness of said blade varying along the longitudinal extent. Auxiliary channels with an advantageous design and orientation can be implemented next to the main channel, improving the functionality. For example, this relates to the advantageous arrangement of light sources or light guides for illuminating the observed point in the body, with the observation usually being implemented through the main channel.

The blade is essentially created integrally by way of additive manufacturing. This allows a variation in wall thickness. This may lead to portions potentially under high loads having greater wall thicknesses than portions subjected to lower loads. Further, the component can be made thicker locally in a targeted fashion for the purpose of reducing the injury tendency, in order to bring about a behaviour that is as atraumatic as possible.

Having said that, a reduction in weight, accompanied by reduced material requirements, can be obtained by way of the new design. This also yields the substantially reduced post-processing complexity. The intention is to avoid a complex assembly of individual parts and hence prevent the risk of deposits at the assembly points.

The blade is essentially created by way of additive manufacturing. However, this does not preclude possible post-processing. For example, post-processing comprises smoothing or locally ablating post-processing. For example, the goal of the post-processing lies in the creation of the desired surface quality and, optionally, a reduction in porosity.

Within the scope of the present disclosure, the term "distal" relates to that portion/region of the instrument which is distant from the user. In other words, a distal end of the instrument, for example a laryngoscope, is regularly inserted into the body interior during the medical procedure. Within the scope of the present disclosure, the term "proximal" relates to a portion/region of the instrument which is distant from the distal end and close to the user. This may comprise designs in which, during the medical procedure, the distal end is arranged within the body and the proximal end is arranged outside of the body. However, this should not be construed as restrictive.

According to an exemplary configuration, the main channel extends between two auxiliary channels which are integrated in the base body, opposite one another and designed to be symmetric with respect to one another in relation to the main channel along a longitudinal extent of the base body in particular. For example, the two auxiliary channels are designed to be symmetric with respect to a central plane through the main channel, with the central plane being parallel to the major axis of the distal end profile.

According to a further exemplary configuration, a longitudinal central plane parallel to the major axis of the proximal end profile extends through the base body, wherein the longitudinal central plane intersects the main channel and the auxiliary channels. Usually there are two longitudinal central planes, one of which is oriented parallel to the major axis of the proximal end profile and another one is oriented parallel to the major axis of the distal end profile.

According to a further exemplary configuration, the base body has a closed profile, at least at the proximal end or at the distal end and preferably at the proximal end and at the distal end. Thus, according to this configuration, the base body lacks a lateral slot through which instruments or the like can be inserted. In the distal end region and in the proximal end region there are respective openings which are respectively aligned substantially distally and proximally. By preference, the base body is closed-off therebetween.

Instruments are insertable through the main channel, and a direct observation is also possible. For example, the at least one auxiliary channel serves to receive illumination technology or serves to receive a light guide. The course of the auxiliary channel follows the course of the main channel, at least in the proximal end region.

According to a further exemplary configuration, the at least one auxiliary channel is separated from the main channel at the proximal end and opens into the main channel at an acute angle in the distal end region. For example, an acute angle comprises an angle (with respect to the respective longitudinal extent) of more than 5° to approximately 45°, for example an angle of less than 30°.

Such designs are obtainable only with great difficulties in the case of a "built" design of the blade. The integral design allows the transition (the opening) between the at least one auxiliary channel and the main channel to be optimized. For example, the at least one auxiliary channel is oriented in such a way in relation to the main channel that, during application, light is directed in the direction of the centre of the distal end profile. This allows an advantageous alignment of the light cone.

According to a further exemplary configuration, the at least one auxiliary channel runs in a straight line next to the main channel, at least in an internal portion between the proximal end region and the distal end region. In this way, the installation space requirements overall can be kept small.

According to a further exemplary configuration, the distal end profile of the base body is widened distally, with this comprising in particular a distally progressive widening. Widening the distal end profile allows a larger viewing angle, with the result that a larger region can be illuminated and observed.

According to specific exemplary configurations, the widening of the base body in the distal end region is progressive, at least on its outer side. In other words, the slope of the widening is not constant but gradually increasing.

In the direction of the distal end, the base body is widened at least approximately in the form of a funnel. This facilitates the application of the instrument.

According to a further exemplary configuration, at least the proximal end profile of the base body is widened proximally, with this comprising in particular a proximally progressive widening. Therefore, the proximal end of the blade may also have a funnel-shaped design overall.

According to a further exemplary configuration, the base body has an atraumatic thickening at least at the distal end, and so the base body has an increased wall thickness in the distal end profile. In particular, the atraumatic thickening has an increased edge radius at a distal end face. This reduces the risk of injury to the patient when the instrument is applied. By way of example, the atraumatic thickening can be designed as a circumferential bead at the distal end of the blade. The atraumatic thickening is advantageously rounded-off in order to avoid contact between sharp-edged/ thin-walled parts and human tissue.

According to a further exemplary configuration, the base body is tapered between the distal end profile and the proximal end profile. This facilitates the handling and application of the instrument.

According to a further exemplary configuration, the distal end profile is oval. In particular, the distal end profile is ovoid or cam shaped. The distal end profile is advantageously adapted to the anatomical design of the vocal cords. By way of example, the region with significant curvature (small local radius) is formed on the side on which the handle is assembled on the blade. By way of example, the distal tip of the blade is also situated in this region with significant curvature.

According to a further exemplary configuration, a minor axis of the proximal end profile is greater than the major axis of the distal end profile, wherein the minor axis of the proximal end profile, as viewed along a longitudinal extent of the base body, is located in a plane together with the major axis of the distal end profile. Hence, the blade is advantageously adapted to the anatomy of the patient and to functional requirements, both at the distal end and at the proximal end.

According to a further exemplary configuration, the distal end profile, in the case of a projection on a plane which is at the distal end and perpendicular to the longitudinal extent of the base body, takes up an area encompassing less than one third of an area of a projection of the proximal end profile on a plane which is at the proximal end and perpendicular to the longitudinal extent of the base body. In the case of a straight longitudinal extent with an appropriate longitudinal axis, the projection planes are parallel to one another. In the case of a (slightly) curved longitudinal extent, the projection planes are optionally oriented at a small angle relative to one another.

According to a further exemplary configuration, the distal end profile, when viewed along a longitudinal extent of the base body, is virtually completely covered by the proximal end profile. However, this should not be construed as restrictive.

According to a further exemplary configuration, the main channel has an oval or round cross section into which the auxiliary channel opens at the inner opening of the at least one auxiliary channel in the base body.

According to a further exemplary configuration, the main channel and the at least one auxiliary channel comprise access openings in the proximal end region, at least portions of said access openings being located in a common plane. The common plane can be jointly manufactured additively.

According to a further exemplary configuration, the main channel comprises a circumferential wall in the base body, wherein at least portions of the at least one auxiliary channel are adjacent to the main channel and said at least one auxiliary channel comprises a circumferential wall, and wherein at least portions of the circumferential walls of the at least one auxiliary channel and main channel intersect in an intersection region.

The intersection ensures that the material use overall is reduced, without this resulting in disadvantages in terms of solidity. Such an intersection within the sense of mutual penetration is not achievable, or only achievable with significant outlay, using conventional approaches for manufacturing such blades.

According to a further exemplary configuration, the intersection region has a thickness along the longitudinal extent between the at least one auxiliary channel and the main channel, said thickness being the same as a thickness of an adjacent portion of the circumferential wall of the main channel. In other words, the circumferential wall of the at least one auxiliary channel is pressed into or embedded in the circumferential wall of the main channel there. In an exemplary configuration, an inner face of the auxiliary channel is tangential to an (imaginary) outer contour of the circumferential wall of the main channel in the intersection region.

According to a further exemplary configuration, a transition between the circumferential walls of the at least one auxiliary channel and main channel is designed to be groove-free. Within the scope of the present disclosure, groove-free means that no chamfer is present. Instead, such regions are advantageously filled with material. This increases stiffness and reduces the tendency to dirty. The risk of foreign bodies being caught is also reduced. The angle of abutting faces is greater than 90°, optionally in the case of an infinitesimal consideration.

According to a further aspect, the present disclosure relates to a surgical laryngoscope having a blade according to at least one of the configurations described herein, wherein a handle for handling the surgical laryngoscope is fastened to the blade. In particular, the handle is oriented at an obtuse or right angle in relation to the main direction of extent of the blade and connected to the base body in the proximal end region. In an exemplary configuration, the handle is an assembly part. In the case of an exemplary configuration, the handle is an integral constituent part of an integral surgical laryngoscope manufactured by means of AM.

According to a further aspect, the present disclosure relates to a method for producing a medical instrument in the form of an integrally designed surgical laryngoscope blade according to at least one of the configurations described herein, including the following steps:

providing a data embodiment of a shaft of the surgical laryngoscope blade, manufacturing the shaft integrally in an additive manufacturing method on the basis of a powdery metallic initial substance while giving due consideration to the data embodiment, and connecting the shaft to a handle at the proximal end of the base body of the shaft.

The method is suitable, in particular, for producing a surgical laryngoscope or the blade thereof according to at least one of the above-described configurations. Additive manufacture allows great freedom of design, with the result that the base body, in particular the entire blade, can be completely or largely designed in integral/one-piece fashion. Various channels can be introduced into the base body despite the integral design; further, it is possible to create internal openings between the channels.

Further, the additive manufacturing enables smooth transitions between various design elements, whereby cleaning/ preparation is further simplified.

According to an exemplary configuration of the method, the step of additively manufacturing the blade comprises a production on the basis of a powdery, austenitic, stainless steel material. Such a material is suitable for medical applications. Thus, there is good patient tolerance. Further, such materials are suitable for cleaning/preparation between various applications. By way of example, the material can be a stainless steel with the material number 1.4404. Such stainless steels have high corrosion resistance.

According to a further exemplary configuration of the method, the manufacturing step comprises the use of a powder bed-based additive manufacturing device, the powder being softened and joined as a result of high-energy radiation in a build chamber of the device. By way of example, this may relate to an SLM (selective laser melting) method. In principle, an SLS (selective laser sintering) method is also conceivable. Both are so-called powder bed methods.

In the case of the SLM method, the material is available in powder form, with substance being conveyed from a storage chamber to a build chamber and being deposited there layer-by-layer, and a platform lowerable by the thickness of a layer in each case being provided in the build chamber. The respective uppermost layer is at least partly fused using a laser beam, with the result that, layer-by-layer, a solid component with the desired geometry is created overall. Regions in which the powder is not fused are cleaned following the construction, with the result that, as a result, the largely or completely finished component with the desired cavities/channels is present.

According to a further exemplary configuration of the method, the base body is manufactured standing up, with a vertical orientation of a longitudinal axis in relation to the build platform. Cross-sectional regions ("slices") of the base body are manufactured simultaneously or at least with a time overlap. This yields sufficiently homogeneous properties in the respective cross-sectional region.

According to a further exemplary configuration of the method, the step of providing the data embodiment comprises a provision of a data embodiment that anticipates an expected warpage of the component during the manufacture. In other words, the warpage of the component can be predicted on account of experience and/or simulations, with the result that the warpage can be "available". If a component artificially warped in the opposite direction now forms the basis of the production and the expected warpage sets in, then this yields the desired design as a result.

A data embodiment is a digital image representation of the design of the component. The digital image representation can be supplemented with further manufacturing information. According to an exemplary configuration of the method, warpage arising on account of inhomogeneous material distributions or material accumulations is taken into account when providing the data embodiment that anticipates the expected warpage.

According to a further exemplary configuration, the method also comprises at least one ablating post-processing step which for example comprises flow grinding of at least the main channel or of the at least one auxiliary channel. In flow grinding, grinding means are driven by a fluid flow and moved along the workpiece. The desired surface quality can thus be created in the channels.

It will be appreciated that the features of the invention mentioned above and the features of the invention yet to be explained below are applicable not only in the respectively specified combination but also in other combinations or on their own, without departing from the scope of the present invention.

Figure 2:
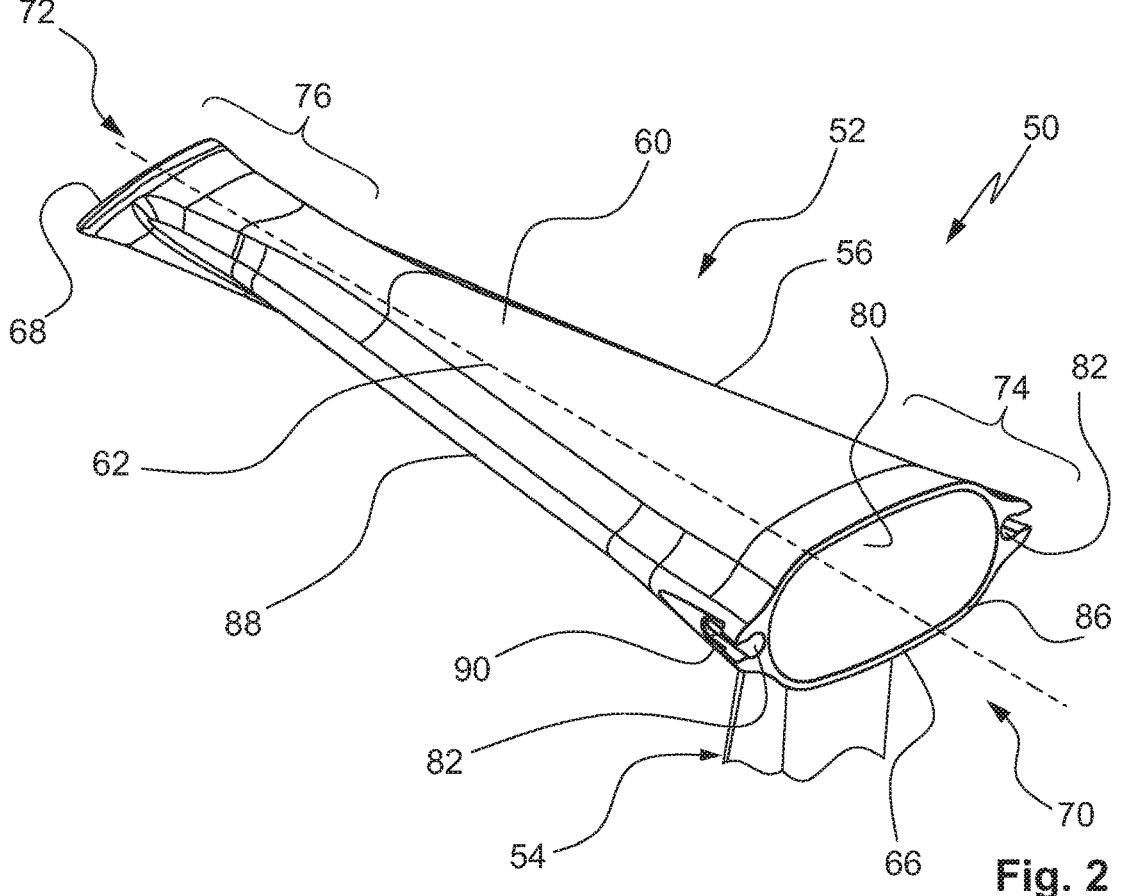
Figures 3, 4:
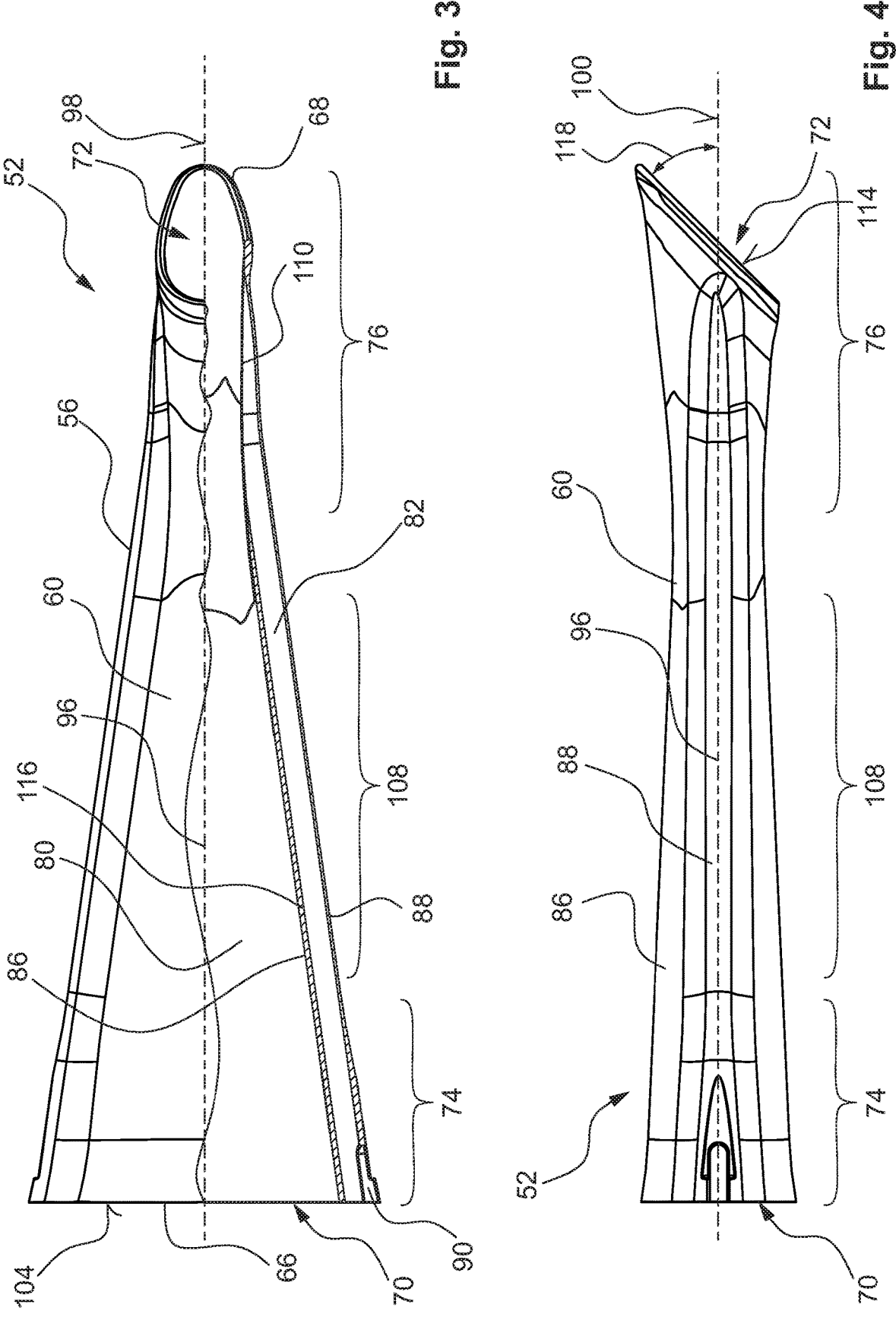
Figure 5:
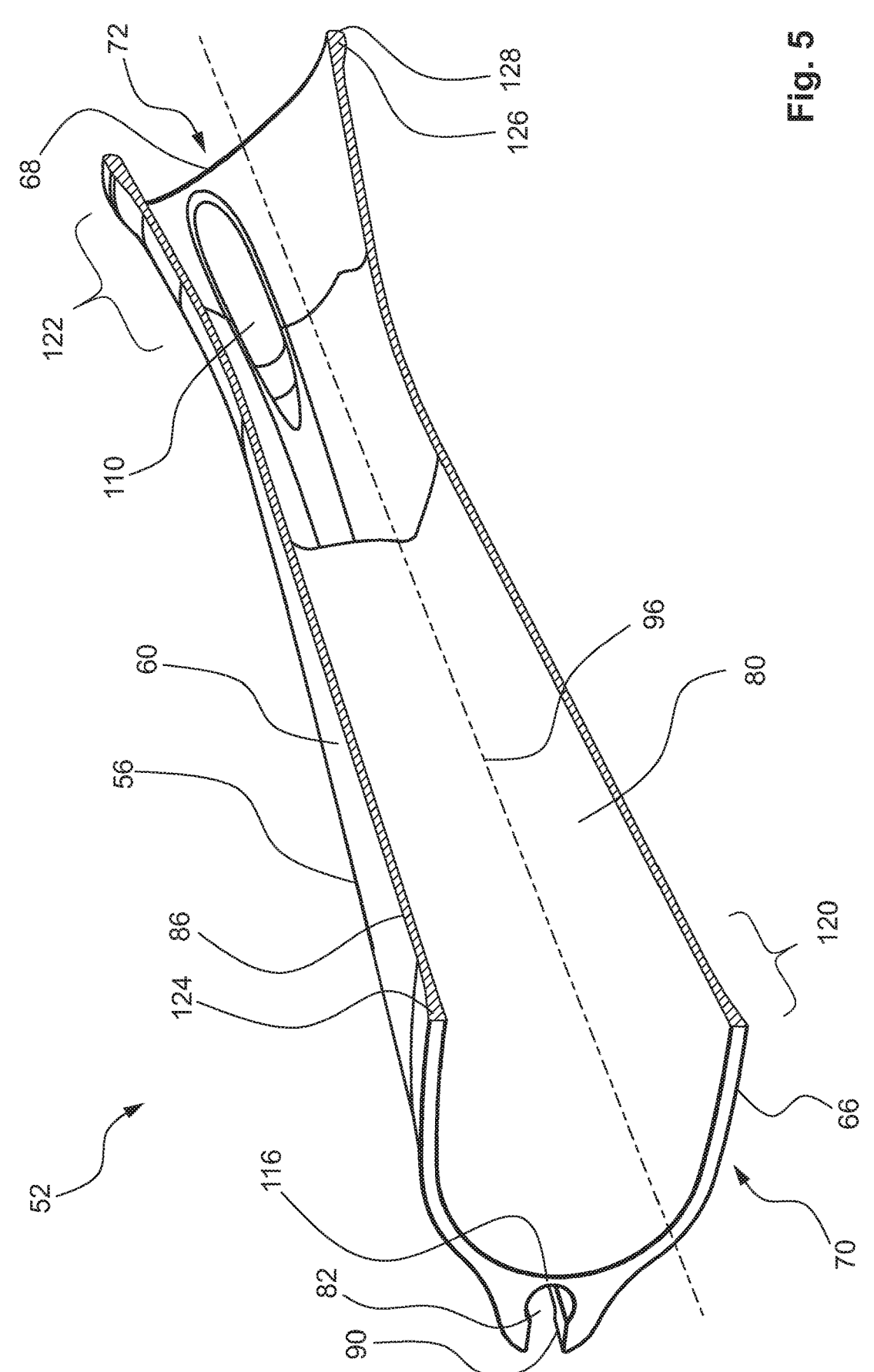
Figure 10:
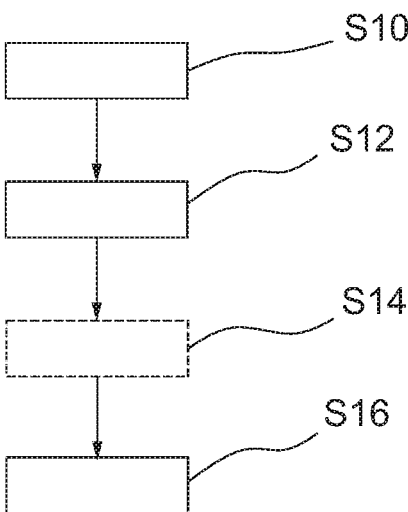

Further features and advantages of the invention arise from the following description of a plurality of preferred exemplary embodiments, with reference being made to the drawings. In detail:

FIG. 1: shows a perspective rearward view of a proximal end of a blade of an instrument in the form of a surgical laryngoscope, with a conventional design;

FIG. 2: shows a perspective rearward view of a proximal end of an additively manufactured blade of a surgical laryngoscope;

FIG. 3: shows a view, cut in half, of the blade according to FIG. 2, wherein the viewing plane is parallel to the longitudinal extent;

FIG. 4: shows a lateral view of the blade according to FIGS. 2 and 3, wherein the orientation of the view is rotated through 90° vis-à-vis the arrangement of FIG. 3;

FIG. 5: shows a perspective rearward view of the blade, from the proximal end, wherein the blade is cut in half for the purposes of elucidating the design of a main channel;

FIG. 6: shows a rearward partial view of the proximal end of the blade in an orientation similar to the orientation according to FIG. 5;

FIG. 7: shows a half view of a proximal end of the shaft;

FIG. 8: shows a half view of a distal end of the shaft, with the orientations of the views according to FIG. 7 and FIG. 8 being opposite to one another;

FIG. 9: shows a sectional view based on FIG. 8 for elucidating a cross section of the shaft in the region of an internal opening; and FIG. 10: shows a block diagram for elucidating a configuration of a method for producing a medical instrument.

On the basis of a perspective rearward view, FIG. 1 shows a conventional design of an instrument, denoted by 10 overall, in the form of a surgical laryngoscope.

The surgical laryngoscope 10 comprises a blade 12 that is joined to a handle 14. The blade 12 forms a shaft 16 which encompasses a main channel 18 and at least one auxiliary channel 20. Provision is usually made of two auxiliary channels 20, formed on both sides of the main channel 18. The shaft 16 extends between a proximal end 24 and a distal end 26. The main channel 18 is formed by a piece of tube 30. The auxiliary channels 20 are formed by separate components in the form of pieces of tube 32 and sleeves 34. Thus, at least five parts have to be manufactured and joined to one another for the purpose of forming the blade 12.

A configuration according to the disclosure of an integrally manufactured blade 52 for a surgical laryngoscope 50 is explained with reference to FIGS. 2-9. The surgical laryngoscope 50 also comprises a handle 54 which, as described previously, is connectable to the blade 52 or, optionally, may even be formed as an integral constituent part.

The blade 52 comprises a base body 60 made of a metal material. The base body 60 has a longitudinal extent 62; the longitudinal extent 62 can be strictly linear or slightly curved. The base body extends between a proximal end 66 and a distal end 68. A proximal end profile 70 facing the operator/surgeon is formed at the proximal end 66. A distal end profile 72 which faces the patient and is optionally introduced into the pharynx of the patient is formed at the distal end 68.

A proximal end region of the base body 60 is indicated for illustrative purposes by a curly bracket denoted by 74. A distal region is indicated for illustrative purposes by a curly bracket denoted by 76. A main channel 80 extending from the proximal end 66 to the distal end 68 is formed in the base body 60. Two auxiliary channels 82, which open into the main channel 80 at their distal end, extend adjacent to the main channel 80 in the exemplary embodiment. A circumferential wall 86 extends around the main channel 80. A circumferential wall 88 extends around the respective auxiliary channel 82. At least portions of the circumferential walls 86, 88 penetrate through one another along the longitudinal extent 62. Further, interfaces 90 that may assist with the integration of light guide or the like are formed at the proximal end of the auxiliary channels 82.

FIGS. 3 and 4 each illustrate views in which the longitudinal extent (compare reference sign 62 in FIG. 2) of the blade 52 is linear and parallel to the viewing plane. A respective longitudinal axis 96 extends through the blade 52 parallel to the viewing plane. This should not be construed as restrictive.

An arising first longitudinal central plane 98, which is perpendicular to the viewing plane and parallel to the longitudinal axis 96, is indicated in FIG. 3. An arising second longitudinal central plane 100, which is perpendicular to the viewing plane and parallel to the longitudinal axis 96, is indicated in FIG. 4. The two longitudinal central planes 98, 100 are oriented orthogonal to one another.

A plane 104 embodied by an end face of the proximal end profile 70 is formed at the proximal end 66 of the shaft 52. For illustrative purposes, an interior portion 108 is indicated between the proximal end region 74 and the distal end region 76 and is also shown using a curly bracket.

The view according to FIG. 3 is cut approximately in half, with the result that the course of the main channel 80 and the course of the at least one auxiliary channel 82 become evident. The auxiliary channel 82 opens into the main channel at an opening 110 in the distal end region 76. The auxiliary channel 82 follows the course of the main channel 82 or of the circumferential wall 86 of the latter, at least in an interior portion 108. Since the main channel 80 is widened both in the direction of the proximal end 66 and in the direction of the distal end 68, the main direction of extent of the auxiliary channel 82 runs at an acute angle with respect to the longitudinal axis 96, and not parallel thereto, at least in the interior portion 108.

For example, the arrangement of the auxiliary channel 82 and opening 110 allows an advantageous illumination of an observation plane which is located by the distal end 68 of the instrument and for example arises due to the distal end profile 82.

Between the circumferential wall 86 of the main channel 80 and the circumferential wall 88 of the auxiliary channel 82 there is an intersection region 116, in which the circumferential walls 86, 88 intersect or penetrate into one another. However, the arising wall thickness in the intersection region 116 need not be greater than the thickness of the circumferential wall 86 of the main channel 80. Further thickening is not required there. In other words, the circumferential wall 88 of the auxiliary channel 82 can be embedded in the circumferential wall 86 of the main channel 80 at said location.

By way of reference sign 118, FIG. 4 also illustrates an inclination angle between a distal end face 114 of the distal end profile 72 and the longitudinal central plane 100. In this respect, too, the shaft 52 has an anatomically advantageous design. The inclination angle 118 is approximately 45°, at least in this exemplary embodiment. For example, the inclination angle 118 can adopt values between 30° and 60°. The distal tip of the distal end face 114 is located on that side of the longitudinal central plane 100 on which the handle (compare reference sign 54 in FIG. 2) would also be arranged/formed.

FIG. 5 uses a perspective illustration to elucidate a half section along the longitudinal extent of the blade 52, from the proximal end 66. FIG. 6 shows a perspective partial view with a similar orientation. The sectional plane corresponds to the longitudinal central plane 98 in FIG. 3. The opening 110 of the auxiliary channel 82 into the main channel 80 is quite visible in FIG. 5.

It also emerges from FIG. 5 that the main channel 80 comprises a widening 120 at the proximal end 66 and a widening 122 at the distal end 68. There is progressive thickening 124 at the proximal end 66. There is progressive thickening 126 at the distal end 68, comprising a region of increased wall thickness and a distally increased edge radius 128. The thickening 126 with the radius 128, in particular, is able to improve the atraumatic behaviour of the blade 52 during application.

FIG. 6 elucidates the proximal end profile 70 in the plane 104 at the proximal end 66 of the blade 52 in particular. Access openings 132, 134 are formed in the plane 104. The access opening 132 is associated with the main channel 80. The access openings 134 are associated with the auxiliary channels 82. A groove-free transition 138 is formed between the circumferential wall 86 of the main channel 80 and the circumferential wall 88 of the auxiliary channel 82. There is no deep and pointed transition (within the meaning of a groove) there; instead, a soft transition 138 is provided. This reduces the tendency to dirty.

FIGS. 7 and 8 elucidate, by way of comparison, the geometry of the proximal end profile 70 (FIG. 7) and of the distal end profile 72 (FIG. 8). FIG. 7 shows a half view from the proximal end. FIG. 8 shows a half view from the distal end. The longitudinal axis 96 is in each case perpendicular to the viewing plane. The proximal end profile 70 has a major axis 140 and a minor axis 144. Overall, the proximal end profile 70 has an oval or elliptical design. The major axis 140 is larger than the minor axis 144. In the exemplary embodiment, the major axis 140 is located in the (second) longitudinal central plane 100. In the exemplary embodiment, the minor axis 144 is located in the (first) longitudinal central plane 98.

The distal end profile 72 likewise has an approximately oval design. By way of example, the distal end profile 72 is cam-shaped or ovoid, with a pointier end of an oval longitudinal cross section of the oval pointing downward in the orientation of the view according to FIG. 8. A major axis 142 is present; it labels the greatest extent of the distal end profile 72. In the exemplary embodiment, the major axis 142 is located in the first longitudinal central plane 98. In the exemplary embodiment, the minor axis 146 is located in the second longitudinal central plane 98 and labels a (smaller) extent of the distal end profile 72 perpendicular to the major axis 142. Hence, the distal end profile 72 has a good geometric adaptation to the vocal cords, facilitating an observation and treatment.

FIG. 9 illustrates a section through the shaft 52 approximately in the region of the opening 110 (also compare FIG. 5), with the observation being from the distal side, similar to FIG. 8. In this region, the main channel 80 has an approximately round or oval cross section 150. Further, reference sign 152 in FIG. 9 is used to show a minimum profile which arises at a constriction in the main channel 80 along the longitudinal extent 62 (compare FIG. 2) or the longitudinal axis 96 (compare FIG. 5). Starting at the minimum profile 152, the main channel 80 widens proximally and distally.

With reference to FIG. 10, a block diagram is used to illustrate an exemplary configuration of a method for producing a component for a medical instrument, in particular a shaft-shaped blade with a plurality of channels. The method comprises a step S10, which comprises the provision of a (CAD) data embodiment. The data embodiment can be generated on the basis of a CAD model. The data embodiment is supplied indirectly or directly to an additive manufacturing apparatus in order to be used there as a basis for forming, integrally and in one piece, the base body embodying the shaft, step S12. In particular, the additive manufacturing is carried out by processing a metal material, for example a stainless steel powder. The base body comprises at least a first channel, a second channel and at least one secondary channel which is adjacent and connected to the second channel. By preference, this creates the base body in a manner requiring little, or possibly even no, post-processing.

This may be followed by an optional step S14. Step S14 comprises post-processing, in particular processing of the surface of at least one of the channels by means of beam grinding. A desired surface quality can be created in this way, for instance in the second channel or in the first channel.

Finally, there is a step S16, which comprises a joining of the shaft with a handle. This may be implemented with the interposition of a connecting piece. This allows an instrument with a complexly designed shaft to be produced in a few steps overall. For instance, this may relate to instruments in the form of surgical laryngoscopes or the blades thereof.

The invention claimed is:

1. A surgical laryngoscope blade integrally made of a metallic base material, having a shaft with an elongate base body which extends between a proximal end and a distal end and which forms a central main channel and two auxiliary channels, at least one auxiliary channel that is usable as a light guide channel, wherein the main channel comprises a proximal end profile at the proximal end and a distal end profile at the distal end, and wherein the main channel extends between the two auxiliary channels which are integrated in the base body, opposite one another and are configured to be symmetric with respect to one another in relation to the main channel along a longitudinal extent of the base body, wherein the proximal end profile has an at least approximately oval design, wherein the proximal end profile has a major axis, wherein the distal end profile has a major axis, wherein the major axis of the proximal end profile and the major axis of the distal end profile are oriented orthogonal to one another, wherein the auxiliary channels are spaced apart from the main channel in a proximal end region adjacent to the proximal end of the base body and open into the main channel in a distal end region adjacent to the distal end, wherein a longitudinal central plane parallel to a major axis of the proximal end profile extends through the base body, and wherein the longitudinal central plane intersects the main channel and the auxiliary channels, wherein the base body has a closed profile, at the proximal and/or distal end, wherein at least one auxiliary channel is separated from the main channel at the proximal end and opens into the main channel at an acute angle in the distal end region, and the auxiliary channels run in a straight line next to the main channel, at least in an internal portion between the proximal end region and the distal end region, wherein the base body is widened distally, and wherein the base body has an atraumatic thickening at least the distal end such that the base body has an increased wall thickness in the distal end profile.

2. The surgical laryngoscope blade of claim 1, wherein at least the proximal end profile of the base body is widened proximally.

3. The surgical laryngoscope blade of claim 1, wherein the base body is tapered between the distal end profile and the proximal end profile.

4. The surgical laryngoscope blade of claim 1, wherein the distal end profile is oval, ovoid, or cam shaped.

5. The surgical laryngoscope blade of claim 1, wherein a minor axis of the proximal end profile is greater than the major axis of the distal end profile, and wherein the minor axis of the proximal end profile, as viewed along a longitudinal extent of the base body, is located in a longitudinal central plane together with the major axis of the distal end profile.

6. The surgical laryngoscope blade of claim 1, wherein the distal end profile, in the case of a projection on a plane which is at the distal end and perpendicular to the longitudinal extent of the base body, takes up an area encompassing less than one third of an area of a projection of the proximal end profile on a plane which is at the proximal end and perpendicular to the longitudinal extent of the base body.

7. The surgical laryngoscope blade of claim 1, wherein the main channel has an oval or round cross section into which the auxiliary channels open at the inner opening of each of the auxiliary channels in the base body.

8. The surgical laryngoscope blade of claim 1, wherein the main channel and the auxiliary channels comprise access openings in the proximal end region, at least portions of said access openings being located in a common plane.

9. The surgical laryngoscope blade of claim 1, wherein the main channel comprises a circumferential wall in the base body, wherein at least portions of the auxiliary channels are adjacent to the main channel and the auxiliary channels each comprise a circumferential wall, and wherein at least portions of the circumferential walls of the auxiliary channels and main channel intersect in an intersection region.

10. The surgical laryngoscope blade of claim 9, wherein the intersection region has a thickness along the longitudinal extent between the auxiliary channels and the main channel, said thickness being the same as a thickness of an adjacent portion of the circumferential wall of the main channel.

11. The surgical laryngoscope blade of claim 9, wherein a transition between the circumferential walls of the auxiliary channels and main channel are designed to be groove-free.

12. A method for producing a medical instrument in the form of an integrally designed surgical laryngoscope blade, the laryngoscope blade comprising a shaft with an elongate base body that extends between a proximal end and a distal end and which forms a central main channel and at least one auxiliary channel that is usable as a light guide channel, wherein the main channel comprises a proximal end profile at the proximal end and a distal end profile at the distal end, wherein the proximal end profile has an at least approximately oval design, wherein the proximal end profile has a major axis, wherein the distal end profile has a major axis, wherein the major axis of the proximal end profile and the major axis of the distal end profile are oriented orthogonal to one another, and wherein the at least one auxiliary channel is spaced apparat from the main channel in a proximal end region adjacent to the proximal end of the base body and opens into the main channel in the distal end region adjacent to the distal end; the method including the following steps:

providing a data embodiment of a shaft of the surgical laryngoscope blade, manufacturing the shaft integrally in an additive manufacturing method on the basis of a powdery metallic initial substance while giving due consideration to the data embodiment, and connecting the shaft to a handle at the proximal end of the base body of the shaft.

13. A surgical laryngoscope blade integrally made of a metallic base material, comprising a shaft with an elongate base body extending between a proximal end and a distal end and that forms a central main channel and at least one auxiliary channel, wherein the main channel comprises a proximal end profile at the proximal end and a distal end profile at the distal end, wherein the proximal end profile has an at least approximately oval design with a major axis, wherein the distal end profile has a major axis, wherein the major axis of the proximal end profile and the major axis of the distal end profile are oriented orthogonal to one another, wherein the at least one auxiliary channel is spaced apart from the main channel in a proximal end region adjacent to the proximal end of the base body and opens into the main channel in a distal end region adjacent to the distal end, wherein the distal end profile is oval, ovoid, or cam shaped, wherein the main channel comprises a circumferential wall in the base body and wherein at least portions of the at least one auxiliary channel are adjacent to the main channel and, the at least one auxiliary channel comprises a circumferential wall, and wherein at least portions of the circumferential walls of the at least one auxiliary channel and main channel intersect in an intersection region, and wherein a transition between the circumferential walls of the at least one auxiliary channel and main channel is groove free.

14. The surgical laryngoscope blade of claim 13, wherein the main channel extends between two auxiliary channels which are integrated into the base body opposite one another and designed to be symmetric with respect to one another in relation to the main channel along a longitudinal extent of the base body.

15. The surgical laryngoscope blade of claim 14, wherein a longitudinal central plane parallel to the major axis of the proximal end profile extends through the base body, and wherein the longitudinal central plane intersects the main channel and the auxiliary channels.

16. The surgical laryngoscope blade of claim 13, wherein the base body has a closed profile at the proximal and/or distal ends.

17. The surgical laryngoscope blade of claim 13, wherein the at least one auxiliary channel is separated from the main channel at the proximal end and opens into the main channel at an acute angle in the distal end region.

18. The surgical laryngoscope blade of claim 13, wherein the distal end profile of the base body is widened distally.

19. The surgical laryngoscope blade of claim 13, wherein the proximal end profile of the base body is widened proximally.

20. The surgical laryngoscope blade of claim 18, wherein the proximal end profile of the base body is widened proximally.

* * * * *